(12) United States Patent
Olsson et al.

(10) Patent No.: US 10,009,519 B2
(45) Date of Patent: Jun. 26, 2018

(54) SELF-LEVELING CAMERA HEADS

(71) Applicants: Mark S. Olsson, La Jolla, CA (US); Bret D. Lobree, San Francisco, CA (US); David A. Cox, San Diego, CA (US)

(72) Inventors: Mark S. Olsson, La Jolla, CA (US); Bret D. Lobree, San Francisco, CA (US); David A. Cox, San Diego, CA (US)

(73) Assignee: SEESCAN, INC., San Diego, CA (US)

( * ) Notice: Subject to any disclaimer, the term of this patent is extended or adjusted under 35 U.S.C. 154(b) by 0 days. days.

(21) Appl. No.: 15/050,267

(22) Filed: Feb. 22, 2016

(65) Prior Publication Data

US 2017/0026554 A1    Jan. 26, 2017

Related U.S. Application Data

(63) Continuation of application No. 13/974,020, filed on Aug. 22, 2013, now Pat. No. 9,277,105, which is a
(Continued)

(51) Int. Cl.
*H04N 9/47* (2006.01)
*H04N 7/18* (2006.01)
(Continued)

(52) U.S. Cl.
CPC ....... *H04N 5/2252* (2013.01); *G01N 21/8803* (2013.01); *G01N 21/954* (2013.01);
(Continued)

(58) Field of Classification Search
CPC ........... F21W 2131/411; G01N 21/954; G01N 2021/9542; G01N 2021/9548;
(Continued)

(56) References Cited

U.S. PATENT DOCUMENTS 3,576,407 A * 4/1971 Stephens, Jr. ............ G07C 1/02
                                                200/46
3,614,726 A * 10/1971 Richter, Jr. ............ H01R 39/00
                                                310/249

(Continued)

FOREIGN PATENT DOCUMENTS

GB       2342419       4/2000

OTHER PUBLICATIONS

Pearpoint, Ltd., "Large Push-Rod Systems: P415 and P455," Catalog, 2009, pp. 15-16, www.Pearpoint.com.
(Continued)

*Primary Examiner* — Chia-Wei A Chen
(74) *Attorney, Agent, or Firm* — Steven C. Tietsworth, Esq

(57) ABSTRACT

In one embodiment, a mechanically self-leveling camera head includes a rear housing assembly, an illumination window, an illumination window retainer having a forward end for holding the illumination window a threaded coupling ring for having the rear housing assembly screwed over a rear portion of the coupling ring and the illumination window retainer screwed over a forward portion of the coupling ring, and a camera module assembly supported inside the housing.

15 Claims, 18 Drawing Sheets

Related U.S. Application Data continuation of application No. 10/858,628, filed on Jun. 1, 2004, now Pat. No. 8,587,648.

(51) Int. Cl.

| | | |
|---|---|---|
| *H04N 5/228* | (2006.01) | |
| *H04N 5/222* | (2006.01) | |
| *H04N 5/225* | (2006.01) | |
| *G03B 37/00* | (2006.01) | |
| *H04N 5/232* | (2006.01) | |
| *G01N 21/88* | (2006.01) | |
| *G01N 21/954* | (2006.01) | |

(52) U.S. Cl.
CPC ......... *G03B 37/005* (2013.01); *H04N 5/2253* (2013.01); *H04N 5/2254* (2013.01); *H04N 5/2256* (2013.01); *H04N 5/2257* (2013.01); *H04N 5/2259* (2013.01); *H04N 5/23293* (2013.01); *H04N 2005/2255* (2013.01)

(58) Field of Classification Search
CPC .......... H04N 2005/2255; G03B 37/005; G03B 37/02; G02B 6/32; G02B 6/3604
USPC ...................... 348/84, 85; 385/26
See application file for complete search history.

(56) References Cited

U.S. PATENT DOCUMENTS

| | | | | |
|---|---|---|---|---|
| 3,621,475 A * | 11/1971 | Walters | ................... | H01P 1/069 333/1 |
| 3,675,549 A * | 7/1972 | Adair | ....................... | G01C 9/12 396/25 |
| 3,769,710 A * | 11/1973 | Reister | ................ | G01C 21/165 244/175 |
| 4,372,658 A | 2/1983 | O'Connor | | |
| 4,434,427 A * | 2/1984 | Clarke | ................ | G03B 37/005 346/33 P |
| 4,855,838 A * | 8/1989 | Jones | ................... | H04N 5/2251 348/345 |
| 4,989,582 A * | 2/1991 | Sakiyama | ............... | A61B 1/042 348/65 |
| 5,195,392 A * | 3/1993 | Moore | .................... | F16L 55/18 138/97 |
| 5,934,911 A * | 8/1999 | Stout | .................. | H01R 13/5219 439/21 |
| 6,030,339 A * | 2/2000 | Tatsuno | ............. | A61B 1/00195 600/112 |
| 6,080,101 A * | 6/2000 | Tatsuno | ............. | A61B 1/00124 348/65 |
| 6,253,138 B1 * | 6/2001 | Shober | ................... | F16H 59/12 477/34 |
| 6,371,907 B1 * | 4/2002 | Hasegawa | .......... | G02B 23/2476 600/102 |
| 6,611,661 B2 | 8/2003 | Buck | | |
| 6,624,954 B2 * | 9/2003 | Taylor | ...................... | G02B 7/02 359/811 |
| 6,633,328 B1 * | 10/2003 | Byrd | ...................... | H04N 7/183 348/143 |
| 6,793,415 B2 * | 9/2004 | Arbuckle | ............... | F16M 11/10 348/373 |
| 6,805,665 B1 * | 10/2004 | Tatsuno | ............. | A61B 1/00188 600/101 |
| 6,820,653 B1 * | 11/2004 | Schempf | ................. | B08B 9/043 138/97 |
| 7,002,620 B1 * | 2/2006 | Rutledge | ................ | H04N 7/181 175/45 |
| 7,217,045 B2 * | 5/2007 | Jones | ................. | G08B 13/1963 348/373 |
| 7,361,140 B2 * | 4/2008 | Ries | ...................... | G02B 6/3817 600/132 |
| 2002/0087179 A1 * | 7/2002 | Culp | ................... | A61B 17/1626 606/167 |
| 2002/0131781 A1 * | 9/2002 | Buck | ...................... | G03B 17/00 396/419 |
| 2003/0052564 A1 * | 3/2003 | Wilsdorf | ................ | H01R 39/24 310/179 |
| 2003/0092966 A1 * | 5/2003 | Schara | ............... | A61B 1/00183 600/173 |
| 2003/0125606 A1 * | 7/2003 | Amling | ............. | A61B 1/00119 600/109 |
| 2003/0198374 A1 * | 10/2003 | Hagene | ................ | G01N 21/954 382/141 |
| 2004/0004660 A1 * | 1/2004 | Mandal | ............... | E21B 47/0002 348/85 |
| 2004/0021858 A1 * | 2/2004 | Shima | .................. | G01N 21/954 356/241.1 |
| 2004/0083829 A1 * | 5/2004 | Chapman | ................ | F16L 55/26 73/865.8 |
| 2004/0121622 A1 * | 6/2004 | Abouchar | .............. | H01R 39/24 439/13 |
| 2004/0133189 A1 * | 7/2004 | Sakurai | .................. | A61B 34/70 606/1 |
| 2004/0169434 A1 * | 9/2004 | Washington | ........... | H01R 39/24 310/232 |
| 2004/0266257 A1 * | 12/2004 | Ries | ...................... | G02B 6/3817 439/577 |
| 2005/0012426 A1 * | 1/2005 | Angerpointner | ....... | H01R 39/24 310/248 |
| 2005/0152002 A1 * | 7/2005 | Shirakawa | ........... | H04N 1/3871 358/1.18 |
| 2005/0157198 A1 * | 7/2005 | Larner | ................. | H04N 5/2351 348/345 |
| 2005/0230115 A1 * | 10/2005 | Rose | ...................... | E21B 31/00 166/301 |
| 2007/0265031 A1 * | 11/2007 | Koizumi | ............. | H04M 1/0225 455/556.1 |
| 2010/0214306 A1 | 8/2010 | Kim | | |

OTHER PUBLICATIONS

Pearpoint, Ltd., "P571," Specifications, 2007, 2 Pages, www.Pearpoint.com.

Pearpoint, Ltd., "P455: Rotational Twin View Colour Camera," Specifications, 2007, 3 Pages, www.Pearpoint.com.

Ridge Tool Company, "microExplorer Digital Inspection Camera," Operator's Manual, p. 12, Elyria, OH, USA.

* cited by examiner

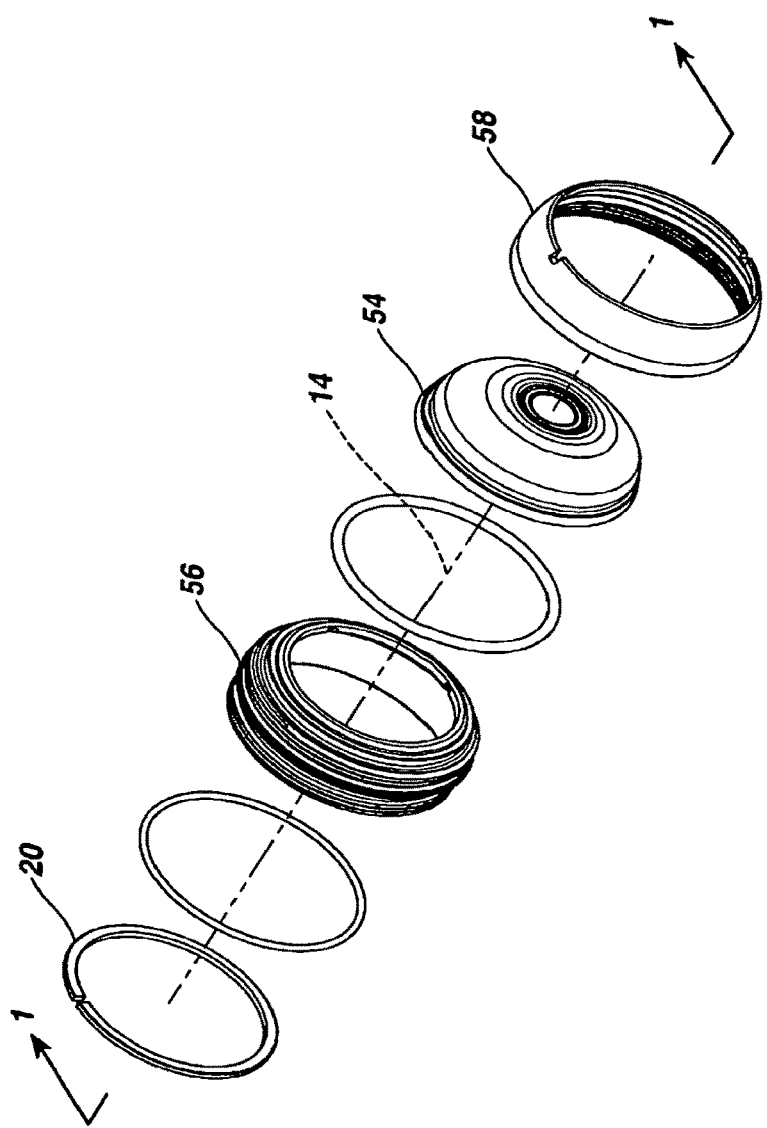

SELF-LEVELING CAMERA HEADS

CROSS-REFERENCE TO RELATED APPLICATIONS

This application is a continuation of and claims priority to co-pending U.S. patent application Ser. No. 13/974,020, entitled SELF-LEVELING CAMERA HEADS, which is a continuation of and claims priority to U.S. patent application Ser. No. 10/858,628, now U.S. Pat. No. 8,587,648 issued Nov. 19, 2013, entitled SELF-LEVELING CAMERA READ. The content of each of these applications is incorporated by reference herein in its entirety for all purposes.

FIELD

This disclosure relates generally to video inspection systems. More specifically, but not exclusively, the disclosure relates to self-leveling camera heads for video pipe inspection systems.

BACKGROUND

There are many applications where a video camera may be used, where the target being observed is not oriented such that it is "upright", i.e. earth normal, in the video scene that is being presented on a monitoring or recording device. Such is often the case in video inspection systems, where a camera is used to look inside of an opening, and the camera may rotate during its traversal towards the observation point. It is also the case where a fixed orientation camera is used to observe variable orientation objects—such as a camera observing a manufacturing process that produces items with variable orientation (such as text printed on bottle caps, which are affixed to bottles, and are being monitored as they roll by). It is further often desirable to orient the video so that it more closely approximates "upright" and normal viewing conditions. This can help to visually orient the viewer, and can help prevent neck strain from having to cock the head to the side to bring the image closer to normal.

Video pipe inspection systems are commonly used to inspect sewer, water and well pipes for blockages and defects. Electrical conduits and other long narrow passages may be similarly inspected. Typically a resilient flexible push cable is pushed down the pipe. A rugged camera head connected to the distal or remote end of the push cable receives power through the push cable. A video signal from an internally mounted video camera sends NTSC or other video signals back through the push cable for display and recording. The camera head is usually centered inside the pipe by radially extending brushes or fins. Alternatively, the camera head may be supported by small wheels that roll along the interior of the pipe. See for example U.S. Pat. No. 6,545,704.

As the camera head snakes its way through the pipe it usually rotates as the push cable twists and turns. The video image follows this motion. Users would prefer a video image that maintains its frame of reference so that the location and nature of defects can be more easily recognized. However, since the camera head is inaccessible after it has been pushed down the pipe, it cannot be manually righted. In some cases, water may be present in the bottom of the pipe, in which case the viewer has a frame of reference, but even then, the periodic twisting of the video image as the camera head moves along the pipe can be very tedious and annoying. Furthermore, water is not always present, or it may fill the pipe entirely. In either of these cases, there is no frame of reference to tell the viewer which part is the top of the pipe.

U.S. Pat. No. 4,372,658 of O'Connor et al. discloses a pipe inspection apparatus in which a camera is supported for rotation by ball bearings mounted within a wheeled housing, and a weight is used to orient the camera. Slip rings are also provided within the housing for transmission of electrical control signals to the camera. This design is not compact and rugged enough for use by plumbers.

UK patent application GB 2 342 419 A filed in the name of Pearpoint Limited on Oct. 5, 1998 and published Apr. 12, 2000 discloses a camera head for pipe inspection in which forward looking and sideways looking cameras are mounted within a rotatable member suspended between bearings at opposite ends of a casing. A motor rotates the member to compensate for motion in the forward looking view. An operator controls the view obtained from the camera head with a keypad and joystick which provides the control signals to the camera head. A commercial version of this camera head incorporates "auto uprighting" of the cameras. The Pearpoint camera head is complex, expensive to manufacture and subject to failures since it lacks the ruggedness required in many pipe inspection applications. The motorized mechanisms take up substantial space inside the camera head, thereby making it difficult to downsize the camera head for inspecting small pipes. Power and control signals must be sent to the motor, requiring extra conductors in the push cable.

U.S. Pat. No. 6,611,661 of Buck discloses a camera head for pipe inspection in which the camera body is mounted for free rotation within a camera housing, and a leveling weight made of tungsten or lead is physically attached to the camera body in a permanent fashion. The center of mass of the weight is displaced from the axis of rotation of the camera body so that the camera body is leveled via gravitational forces. A bearing is positioned between the camera body and the camera housing. A slip ring has portions that fit on inner and outer races of the bearing. However, this design does not lend itself to easy removal and/or repair of the video camera and associated electronics within the camera head.

In the past, there have also been electronic solutions to the problem of orienting a video image from a remote video camera. If one is only interested in a rotation of one hundred and eighty degrees (the coarsest rotation—commonly called a screen flip), this can easily be done in one of two ways. The video transmitted by the camera can be converted to a digital format and re-mapped so that it is presented with what was originally the lower right most pixel, remapped to the upper left most corner, and so on. The remapped digital data can then be reconverted to analog form. Alternatively in the case of a monitor having a cathode ray tube, the vertical and horizontal gun polarity can be reversed. Instead of scanning from left to right, top to bottom, the guns scan right to left, bottom to top. Either approach yields the same effect of rotating the video from the camera by one hundred and eighty degrees.

A digital flip and/or mirror is also commonly used both in LCD monitors as well as in some CCD cameras. One advantage of doing the flip before recording is that the corrected image is then recorded. Pipe inspection systems in use today that invert the image on the monitor do not allow the inverted image to be recorded. The main advantages of the flip approach are low cost and the fact that it preserves the original aspect ratio of the video (typically 4:3). The primary disadvantage is the limited rotational resolution (only offering two positions—0 degrees and 180 degrees of rotation).

Some manufacturers of video equipment have taken a video stream, converted it into a digital format, performed a matrix operation on the digital data to rotate the entire image by a predetermined amount, and then re-converted the digital data to an analog signal. This approach is optimal in terms of the rotational resolution, however it is extremely computationally intense, and therefore requires a significant cost in parts and power. It also suffers from the drawback that the rectangular 4:3 array is clipped so that some video content is lost at any angles other than zero and one hundred and eighty degrees. At rotations of ninety and two hundred and seventy degrees, the entire right and left lobes of the source video are lost.

Accordingly, there is a need in the art to address the above-described as well as other problems.

SUMMARY

In accordance with one aspect of the present invention a self-leveling camera head includes an outer housing and a camera module assembly including an image sensor supported inside the outer housing for free rotation around a first axis. A leveling weight assembly is supported inside the outer housing separate from the camera module assembly for free rotation about a second axis, which preferably substantially coincides with the first axis, as a result of a center of gravity of the leveling weight assembly being displaced from the second axis. The leveling weight assembly is removably coupled to the camera module assembly so that the leveling weight assembly can turn the camera module assembly to a predetermined angular orientation.

In accordance with another aspect of the present invention a camera head includes an outer housing and a camera module assembly including an image sensor supported inside the outer housing for free rotation around an axis. A slip ring assembly includes a connector assembly that removably mates with a contact assembly. The contact assembly is mounted to the camera module assembly for rotation therewith, and the connector assembly is fixedly mounted within the outer housing.

In accordance with yet another aspect of the present invention a camera head includes an outer housing and a camera module assembly including an image sensor supported inside the outer housing for free rotation around an axis. A slip ring assembly includes a first portion mounted to the camera module for rotation therewith and a second portion fixedly mounted within the outer housing. The second portion can be plugged into the first portion along the axis.

The slip ring assembly can be unplugged to allow for repair or replacement of the camera module assembly.

In accordance with still another aspect of the present invention a video pipe inspection system has a camera head including a high resolution image sensing device. A push cable is connected to the camera head. A processing circuit connected to the push cable processes a video signal from the camera head to generate a sub-sampled region and rotates the sub-sampled region into a predetermined orientation for display.

In accordance with still another aspect of the present invention a video pipe inspection system includes a camera head having an image sensing device and a push cable connected to the camera head. An orientation sensor senses an angular orientation of the camera head. A processing circuit is connected to the push cable for processing a video signal from the camera head and an output signal from the orientation sensor so that images that are stored or displayed have a predetermined orientation.

In accordance with another aspect of the present invention a camera head includes a rear housing assembly with a female threaded forward end and an illumination window. The camera head further includes an illumination window retainer having a forward end for holding the illumination window and a female threaded rearward end. A male threaded coupling ring is provided for having the rear housing assembly screwed over a rear portion of the coupling ring and the illumination window retainer screwed over a forward portion of the coupling ring. A camera module assembly is supported inside the enclosure defined by the joining of the rear housing assembly, illumination window, illumination window retainer, and coupling ring.

Various additional aspects, features, and functionality are further described below in conjunction with the appended Drawings.

BRIEF DESCRIPTION OF THE DRAWINGS

The present application may be more fully appreciated in connection with the following detailed description taken in conjunction with the accompanying drawings, wherein:

FIGS. 2A, 2B and 2C collectively form a reduced exploded isometric view of a the self-leveling camera head illustrated in assembled and sectioned form in FIG. 1.

DETAILED DESCRIPTION OF EMBODIMENTS

Figure 1:
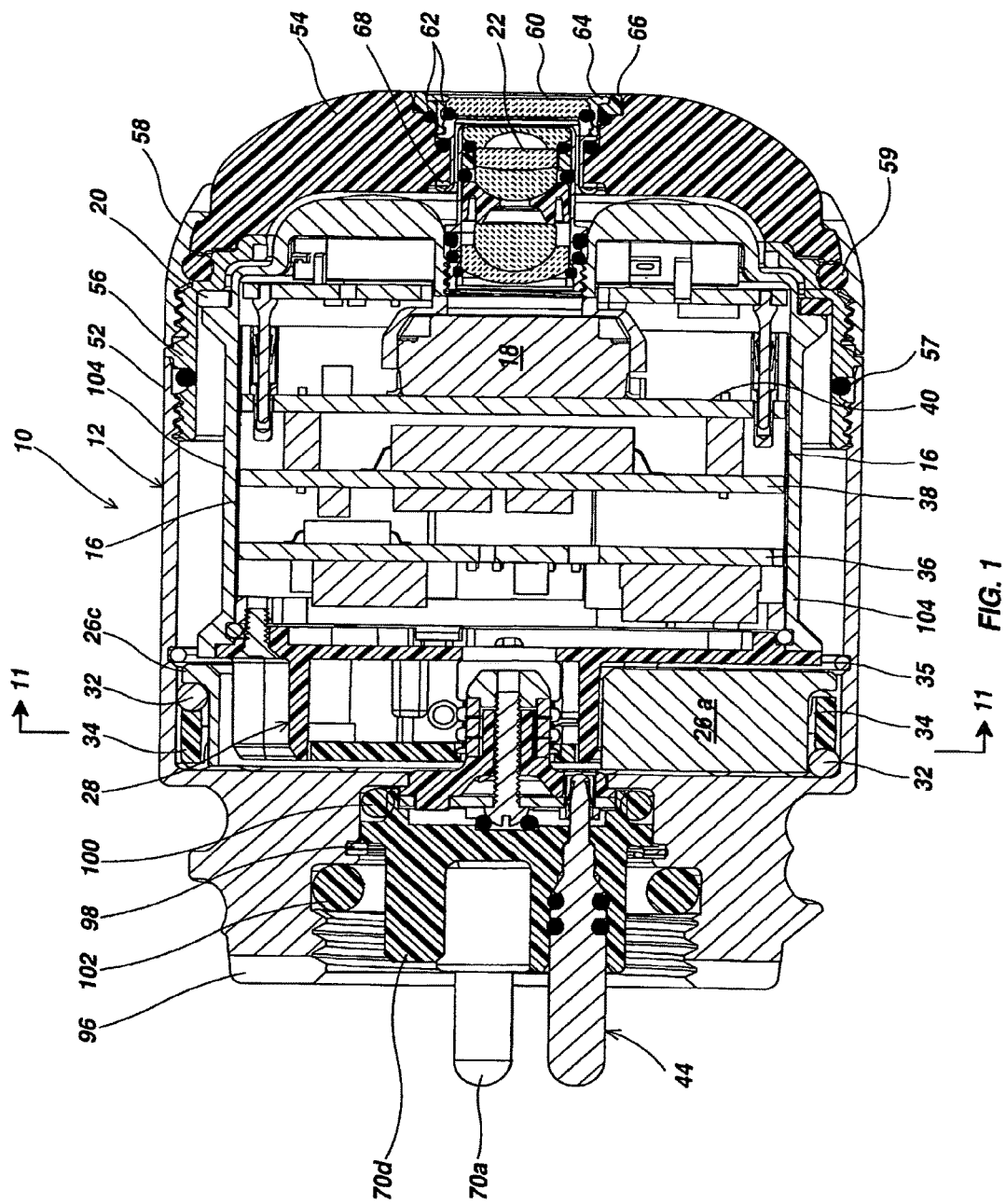
FIG. 1 is an assembled sectional view of an embodiment of a self-leveling camera head in accordance with our invention taken along lines 1-1 of FIGS. 2A, 2B and 2C.
Figure 2B:
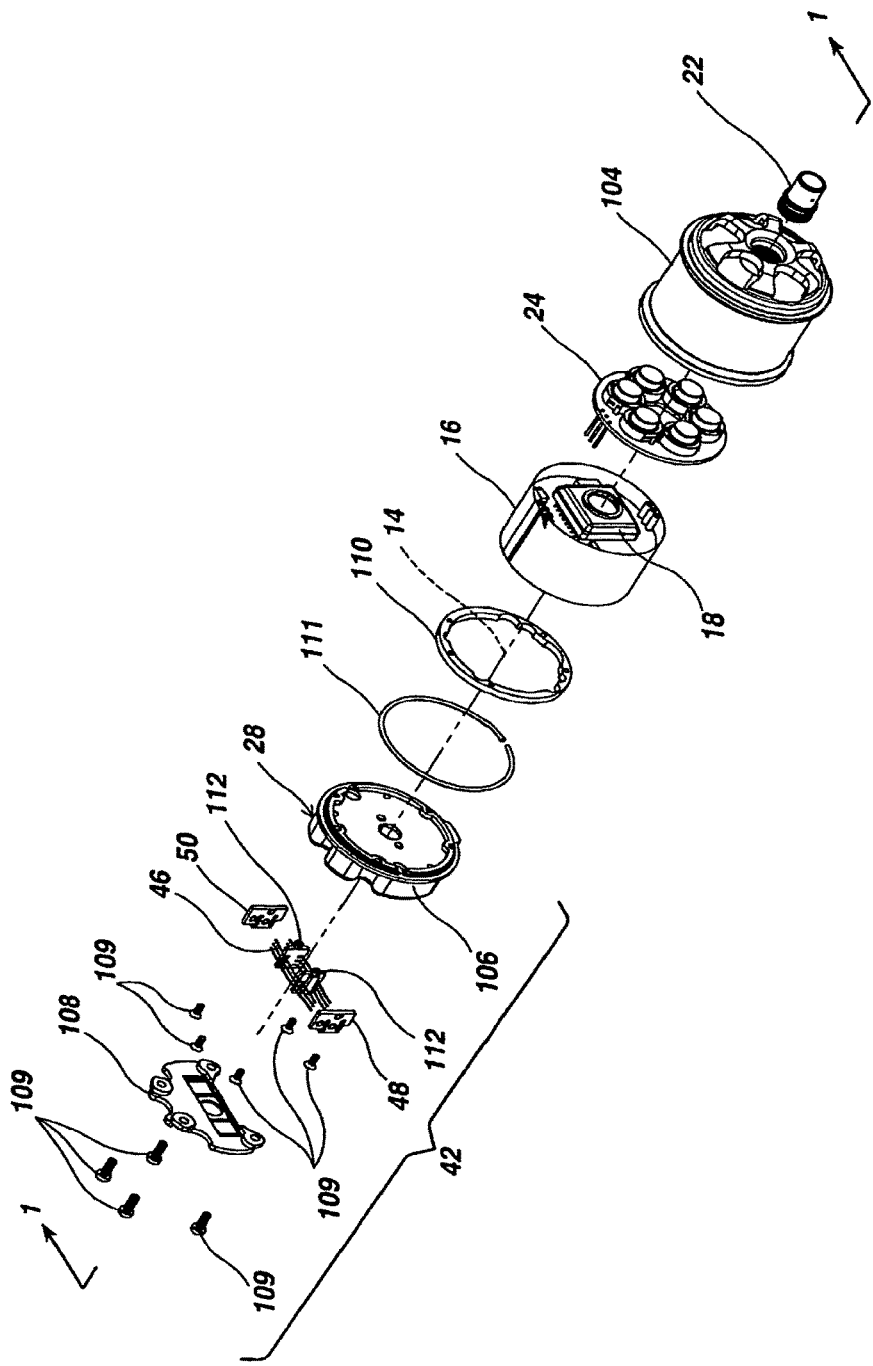
Figure 2C:
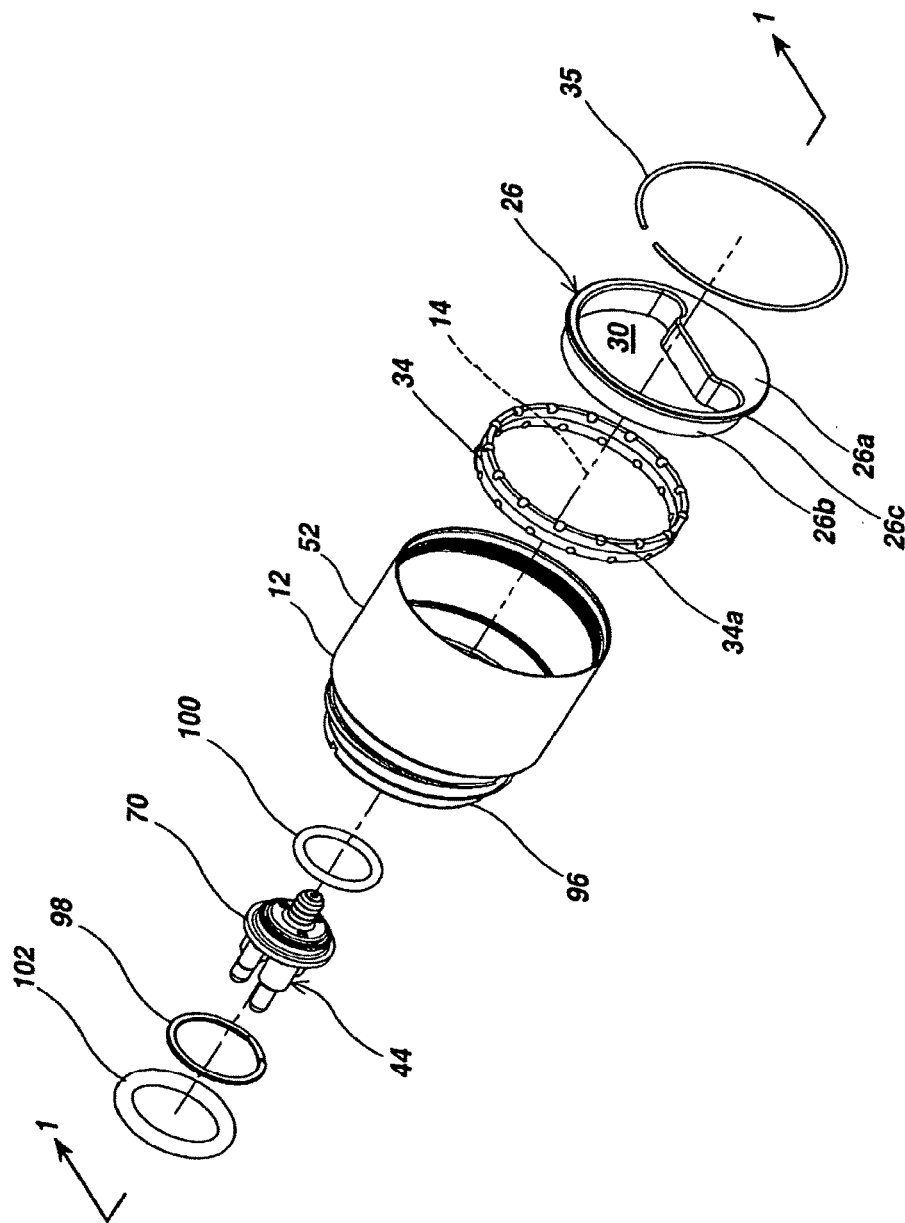
Figure 3:
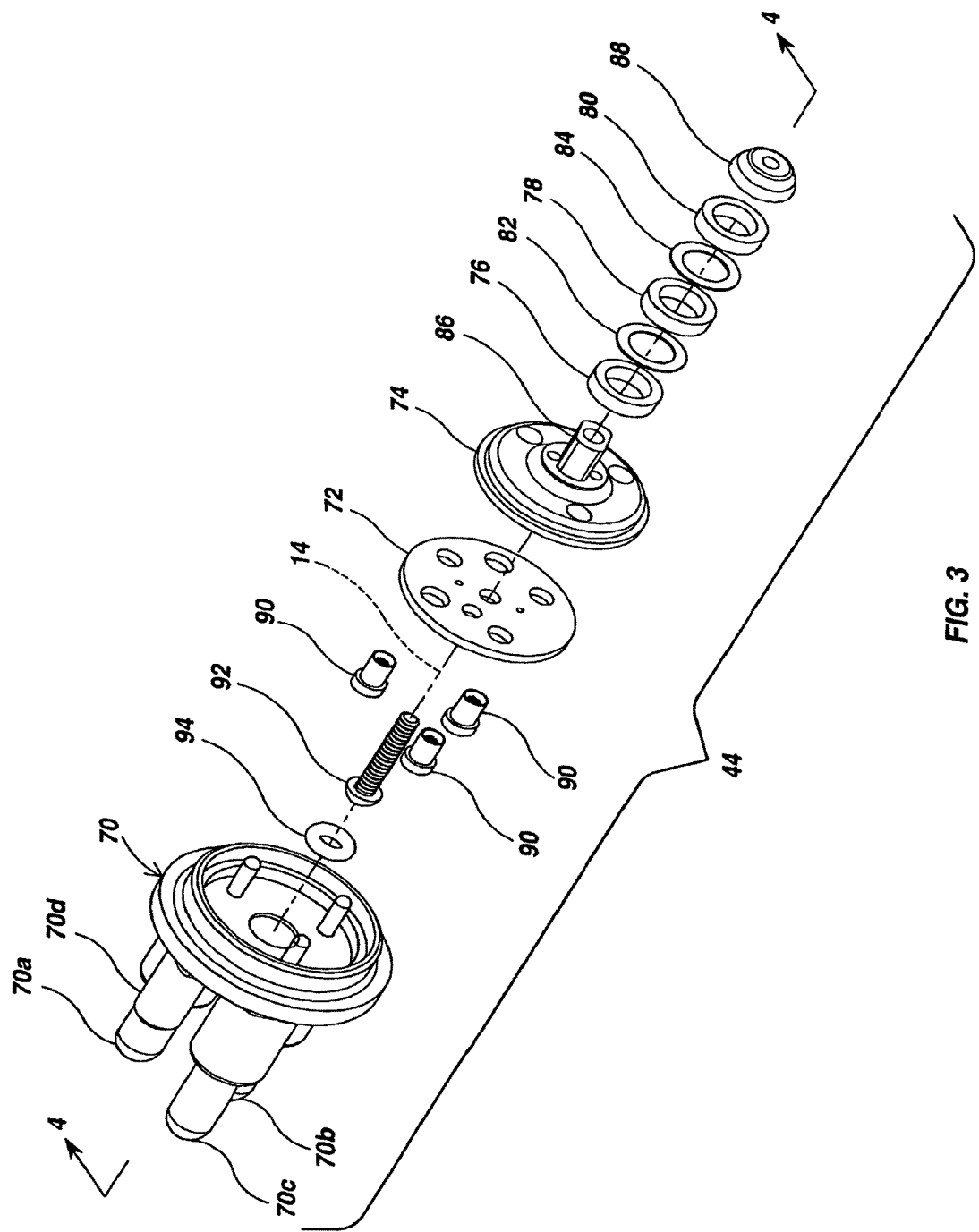
FIG. 3 is an exploded isometric view of the connector assembly of the slip ring assembly of the self-leveling camera head of FIG. 1.
Figure 4:
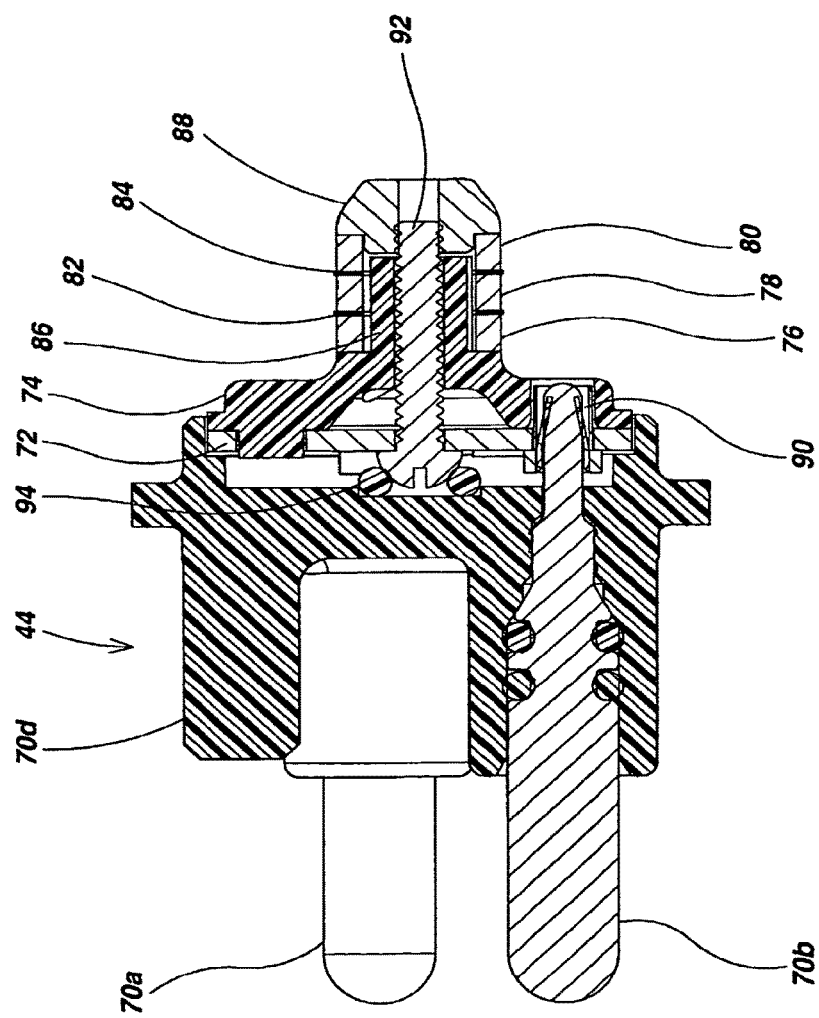
FIG. 4 is an enlarged sectional view of the connector assembly taken along lines 4-4 of FIG. 3.

Referring to FIG. 1, a self-leveling camera head 10 includes a stainless steel generally cylindrical outer housing 12 having a central axis 14 (FIGS. 2A, 2B and 2C). A camera module assembly 16 (FIGS. 1 and 2B) including an image sensor 18 is supported inside the outer housing 12 for free rotation around the central axis 14 via Teflon (trademark) or Teflon composite split-ring bushing 20. Other forms of low friction material may be used to fabricate the bushing 20. The image sensor 18 is preferably a charge coupled device (CCD) and has associated filter elements for producing output signals that represent a color image based on light reflected from scenes and objects within a field of view established by a lens assembly 22 illuminated by an LED assembly 24 (FIG. 2B). The image sensor 18 could also be a CMOS imager.

The lens assembly 22 (FIGS. 1 and 2B) focuses light on the image sensor 18. It is mounted in a threaded assembly so that it can be screwed back and forth along the central axis 14 during factory calibration to ensure that the light is focused in an optimum manner on the image sensor 18. Various O-rings (visible but unnumbered in FIG. 1) ensure that water does not pass into the lens assembly 22.

Figure 6:
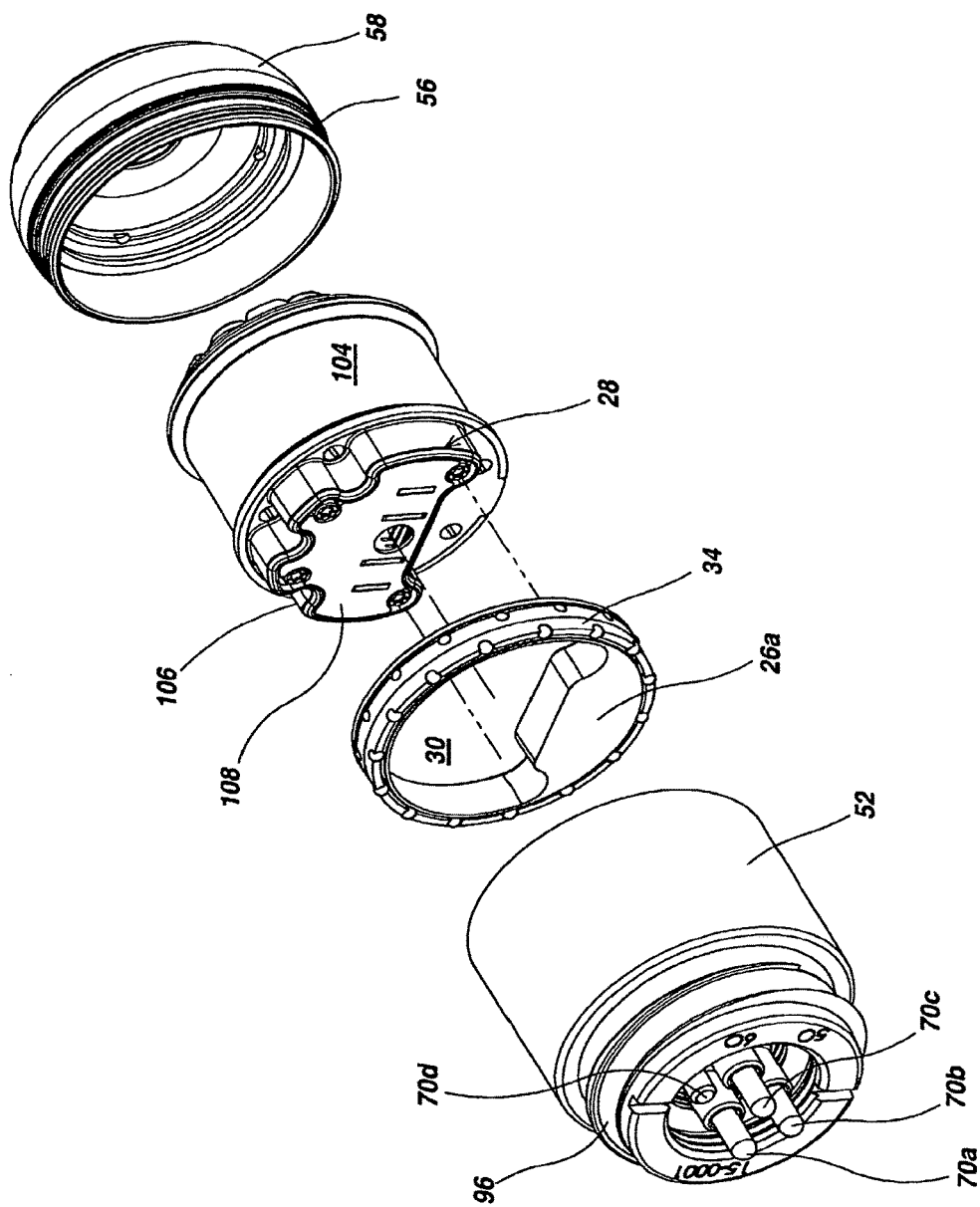
FIG. 6 is an exploded isometric view of the rear housing assembly, ball bearing support, micro slip wire base, micro slip ring rotating can, coupling ring, and LED window of the self-leveling camera head of FIG. 1, illustrating further details thereof.
Figure 7:
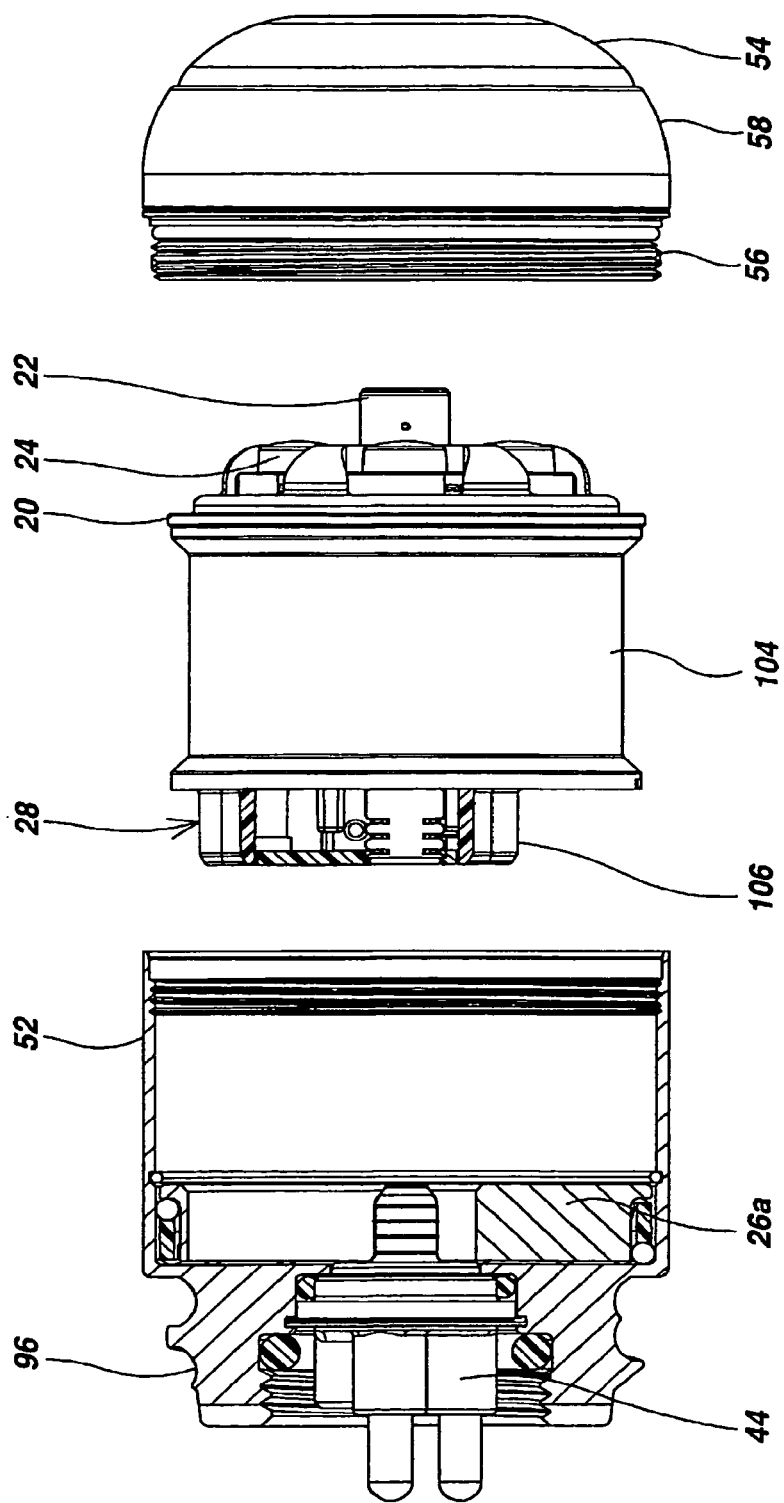
FIG. 7 is an exploded, part elevation, part sectional view of the self-leveling camera head of FIG. 1 illustrating further details thereof.
Figure 8:
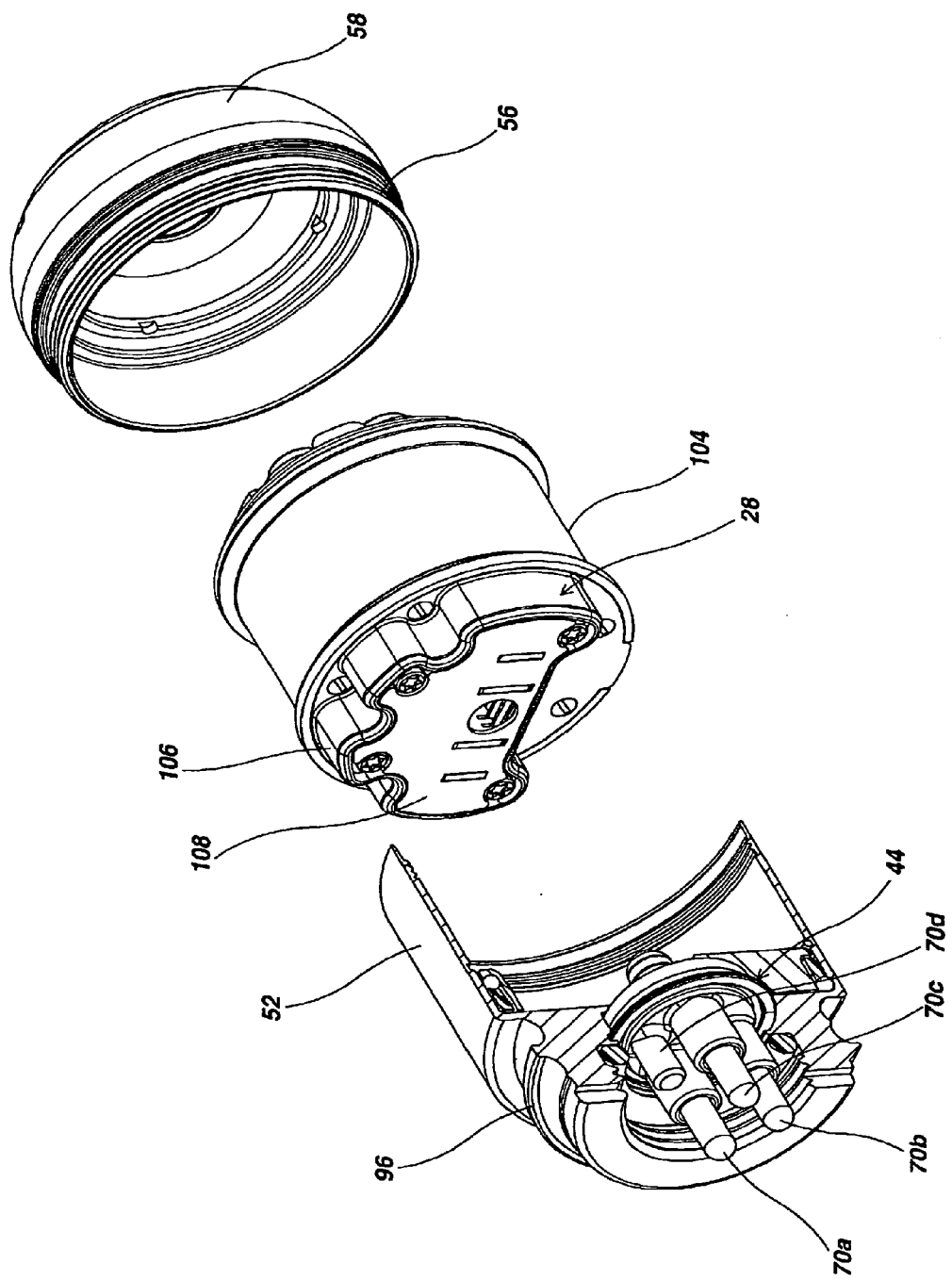
FIG. 8 is an exploded, part sectional, isometric view of the self-leveling camera head of FIG. 1 illustrating further details thereof.
Figure 12:
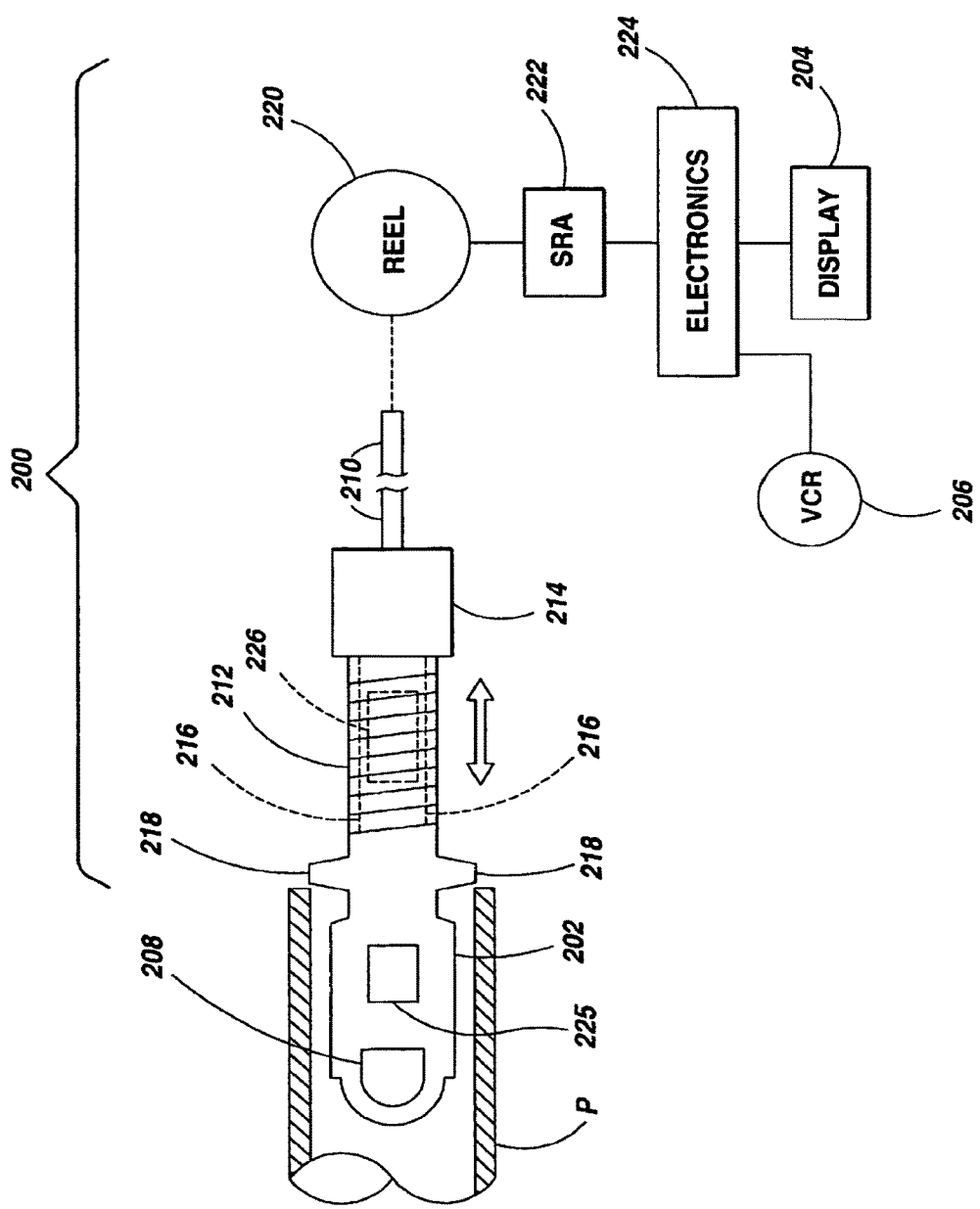
FIG. 12 is a block diagram of a video pipe inspection system that re-orients video images electronically.

A leveling weight assembly 26 (FIG. 2C) is supported inside the outer housing 12 separate from the camera module assembly 16 for free rotation about the central axis 14 as a result of a center of gravity of the leveling weight assembly 26 being displaced from the central axis 14. Means are provided for enabling removable coupling of the leveling weight assembly 26 and the camera module assembly 16 so that the leveling weight assembly 26 can turn the camera module assembly 16 to a predetermined angular orientation as the camera head 10 rotates during insertion into a pipe P (FIG. 12). In the illustrated embodiment, the removable coupling means comprises a key including mating portions of the leveling weight assembly 26 (FIG. 2C) and the camera module assembly 16 (FIG. 2B). These mating portions include a part cylindrical projecting portion 28 (FIGS. 1 and 6-8) on the rear side of the camera module assembly 16 that fits within a similarly shaped opening 30 (FIGS. 2C and 6) in the leveling weight assembly 26.

The lower half-cylinder portion 26a of the leveling weight assembly 26 provides an eccentrically located weight. The leveling weight assembly 26 is preferably made of Tungsten which makes the leveling weight assembly 26 relatively heavy for its size. The remainder 26b (FIG. 2C) of the leveling weight assembly 26 extends around the periphery of the opening 30. Together the portions 26a and 26b provide a round outer peripheral surface. A ball bearing assembly is used to support the leveling weight assembly 26 for free rotation about the central axis 14. One race of the ball bearing assembly is provided by the round outer peripheral surface of the portions 26a and 26b on which a plurality of ball bearings 32 (FIG. 1) roll. A ball bearing support 34 (FIG. 2C) captures the ball bearings 32 in individual curved recesses 34a (FIG. 2C) on one side and holds them in place against a circular flange 26c (FIGS. 1 and 2C) that extends radially from the leveling weight assembly 26. Another race of the ball bearing assembly is provided by the inner surface of the outer housing 12. A snap ring 35 is positioned in a groove formed in the inside wall of the outer housing 12 and is used to hold the leveling weight assembly 26 in place inside the outer housing 12 when the camera module assembly 16 and its supporting structure (hereafter described) are removed from the forward part of the outer housing 12 during service or assembly.

Figure 11:
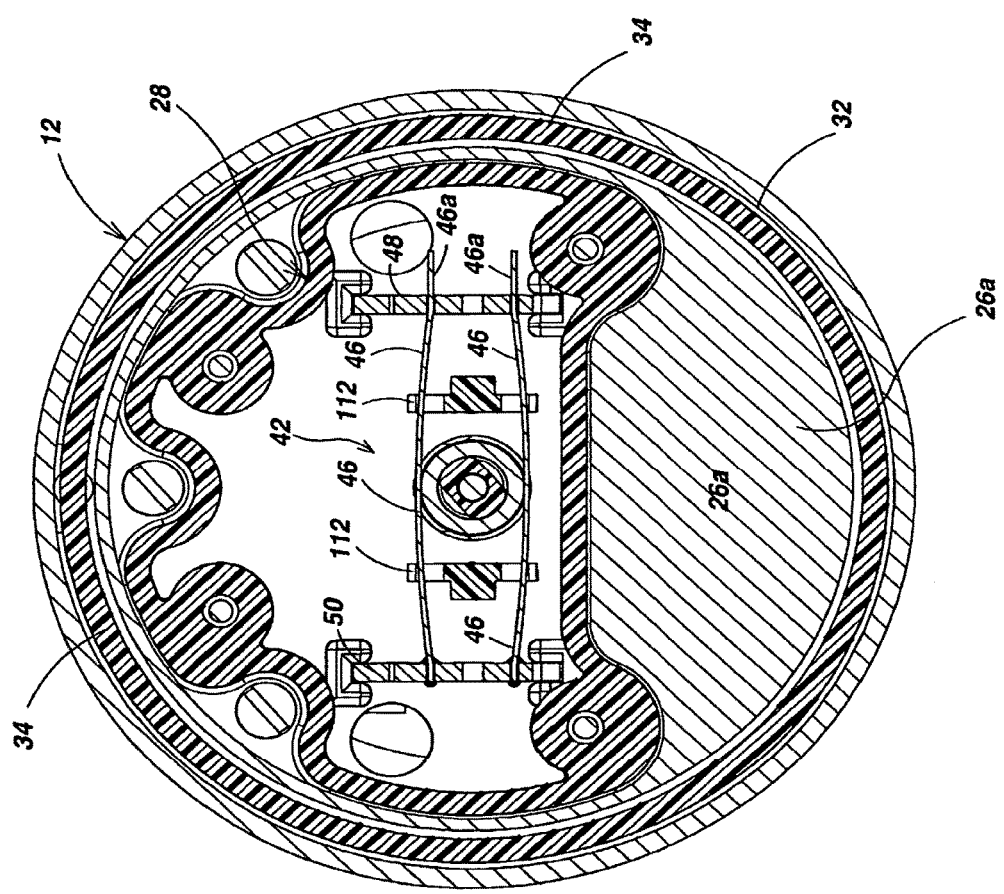
FIG. 11 is an enlarged cross-sectional view of the self-leveling camera head of FIG. 1 taken along lines 11-11 of FIG. 1 illustrating details of its contact assembly.

A slip ring assembly extends through the leveling weight assembly 26 and removably connects to the camera module assembly 16. The slip ring assembly is separable into two portions to allow the camera module assembly 16 to be removed from the forward end of the outer housing 12. This allows the camera module assembly 16 and its associated electronics mounted on circuit board assemblies 36, 38 and 40 (FIG. 1) to be easily repaired and/or replaced. The slip ring assembly includes a contact assembly 42 (FIGS. 2B and 11). A connector assembly 44 (FIGS. 3, 4, 9 and 10) plugs into the contact assembly 42. The contact assembly 42 includes a plurality of resilient, flexible, straight conductive contact brushes 46 (FIGS. 2B and 11) having proximal ends soldered to circuit board assemblies 48 and 50 (FIG. 11).

Figure 5:
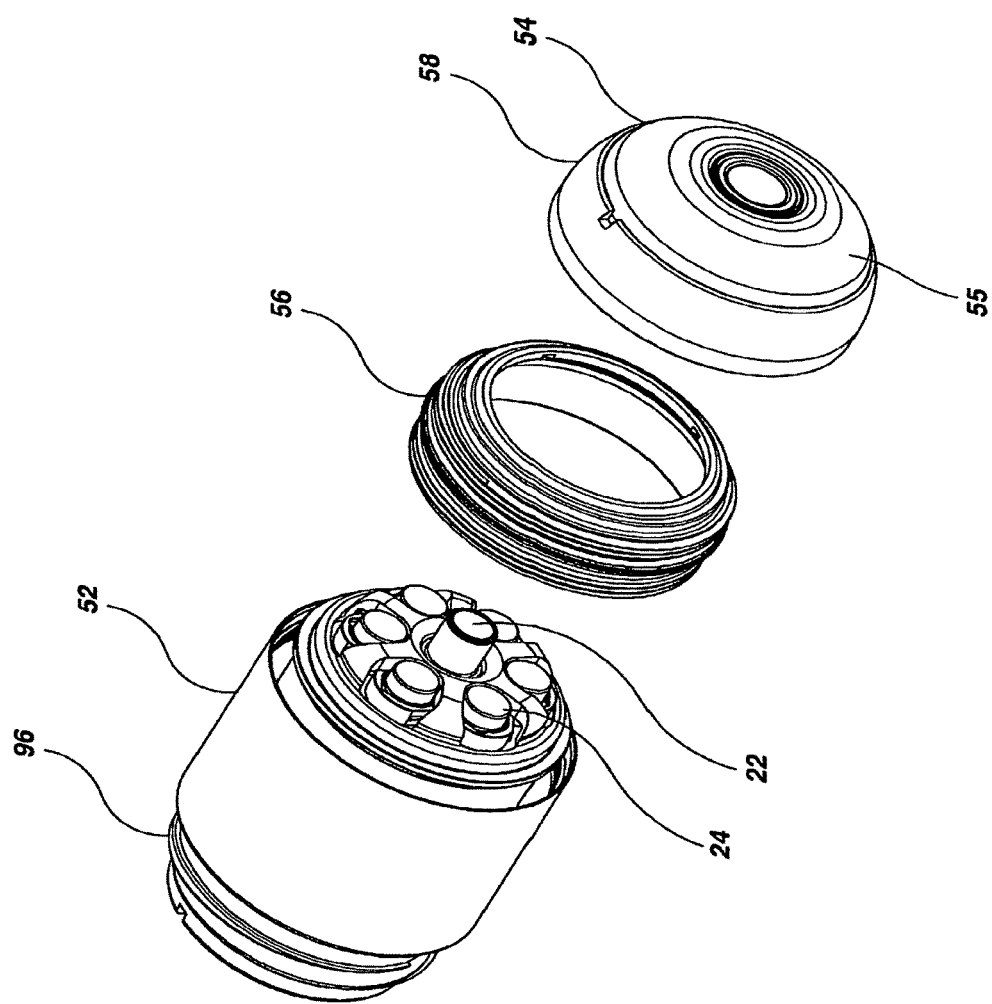
FIG. 5 is an exploded isometric view of the micro slip ring rotating can, coupling ring and LED window of the self-leveling camera head of FIG. 1 illustrating further details thereof.

The outer housing 12 includes an outer cylindrical rear housing assembly 52 (FIG. 2C), a forward LED (illumination) window 54 (FIG. 2A) made of acrylic, Nylon (trademark), polycarbonate or other hard transparent plastic material, and a coupling ring 56. An LED (illumination) window retainer 58 (FIGS. 2A and 5) mates with the coupling ring 56 to retain the LED window 54. The forward end of the LED window retainer 58 has a radially inwardly projecting portion which holds onto a rear shoulder of the LED window 54. In the embodiment illustrated, the coupling ring 56 has male threads formed on its exterior as best seen in FIG. 1. The forward end of the rear housing assembly 52 has female threads formed on its interior so that it can be screwed over the rear portion of the coupling ring 56. Similarly, the rear portion of the LED window retainer 58 has female threads formed on its interior so that it can be screwed over the forward portion of the coupling ring 56. The camera module assembly 16 is thus supported inside the enclosure defined by the joining of the rear housing assembly 52, LED window 54, LED window retainer 58 and coupling ring 56. The coupling ring 56 extends forward of the camera module assembly 16. An O-ring 57 is seated in a groove formed in the coupling ring 56 between the rear portion of its male threads and the forward portion of its male threads and provides a rear watertight seal. Another O-ring 59 provides a forward watertight seal between the LED window 54, LED window retainer 58 and coupling ring 56. The construction of the outer shell of the camera head 10 allows for easy disassembly for repair and provides a large clearance frontal opening away from the attachment of the push cable for installation and removal of the leveling weight assembly 26 and the camera module assembly 16.

A window 60 (FIG. 1) made of a high strength scratch resistant material such as Sapphire is mounted front of the lens assembly 22 in a central aperture in the LED window 54 with O-ring 62 and retainer rings 64 and 66. The window 60 is fixed in place using a tube whose reward flared end is held by a retaining washer 68.

The connector assembly 44 (FIGS. 3 and 4) includes a micro connector plate assembly 70 with male plugs 70a, 70b, 70c and 70d (FIGS. 3 and 6), micro connector circuit board 72, and micro ring base 74 which are assembled along the central axis 14. The large ends of male plugs 70a, 70b and 70c mate with female connectors (not illustrated) in a coupling that screws over the rear end 96 (FIG. 1) of the outer housing 12 in order to transmit electrical signals. The male plug 70d provides a mechanical alignment mechanism. The slip ring assembly may provide an RF connection path via two of the three male plugs 70a, 70b and 70c of the connector assembly 44.

Micro silver graphite rings 76, 78 and 80 (FIGS. 3 and 4) are separated by insulating micro ring spacers 82 and 84 (FIG. 3) and are all held over a rectangular post 86 of the micro ring base 74 by a micro ring cap 88. Three female pin receptacles 90 are positioned in corresponding holes in the micro connector circuit board 72 and micro ring base 74. The pin receptacles 90 receive the forward ends of the male plugs 70a, 70b and 70c. A slotted round head screw 92 screws through a hole in the post 86 and into the micro ring cap 88. An O-ring 94 (FIG. 3) stands off the head of the screw 92 from the micro connector plate assembly 70. The micro plate assembly 70 is captured in a cylindrical recess formed in the rear end 96 (FIGS. 1 and 2C) of the rear housing assembly 52 via snap ring 98. O-rings 100 and 102 (FIG. 2C) provide water tight seals that prevent liquid in the pipe being inspected from entering the outer housing 12 past the micro connector plate assembly 70. The silver graphite rings 76, 78 and 80 are connected via terminals and wires (not illustrated) to the micro connector circuit board 72 (FIG. 3) and the pin receptacles 90.

A cylindrical micro slip ring rotating can 104 (FIGS. 1, 2B, 6 and 7) surrounds and supports the camera module assembly 16 and rotatably slides against the Teflon split-ring bushing 20 at its forward end. The micro slip ring rotating can 104 also carries the lens assembly 22 and the LED assembly 24 (FIG. 2B). The projecting portion 28 (FIG. 7) on the rear side of the camera module assembly 16 includes a micro slip wire base 106 (FIGS. 2B, 6, 7 and 8) and a micro slip wire cap 108 secured together with screws 109 (FIG. 2B). The projecting portion 28 conformably fits within the opening 30 in the leveling weight assembly 26 (FIG. 2C). Thus, during assembly of camera head 10 the connector assembly 44 (FIGS. 3 and 4) plugs into the contact assembly 42 (FIGS. 2B and 11) through the leveling weight assembly 26. The connector assembly 44 and the contact assembly 42 axially mate, i.e. they plug and unplug via relative longitudinal movement along the central axis 14. In addition, at the same time, the leveling weight assembly 26 is coupled to the projecting portion 28 attached to the rear end of the camera module assembly 16 and surrounded by the rotatably supported micro slip ring rotating can 104. A very important advantage of the structure of our camera head 10 is that the connector assembly 44 can be removed from the rear end 96 (FIG. 1) of the rear housing assembly 52 by removing snap ring 98. This can be accomplished without having to remove the leveling weight assembly 26 or the camera module assembly 16. A significant advantage of the configuration of the camera head 10 lies in the fact that its slip ring assembly is modular and is not integrated into or connected to the outer housing 12. This allows its two portions, namely, the contact assembly 42 and the connector assembly 44, to be unplugged and separately removed for ease of service.

The cylindrical micro slip ring rotating can 104 (FIGS. 1 and 2B) can freely rotate against Teflon split-ring bushing 20 about the central axis 14 and the leveling weight assembly 26 can freely rotate against the ball bearings 32 (FIG. 1) about the central axis 14. This allows the leveling weight assembly 26 to turn the camera module assembly 16 under the force of gravity to a predetermined angular orientation, preferably so that the images generated with the output of the image sensor 18 will be upright on a CRT or other display device. The micro slip wire base 106 (FIGS. 2B and 6) is screwed into a micro slip wire base ring 110 (FIG. 2B). The micro slip wire base ring 110 is retained in the slip ring rotating can 104 by a spring wire 111. When assembled, all of the components illustrated in FIG. 2B spin together about the central axis 14.

Figure 9:
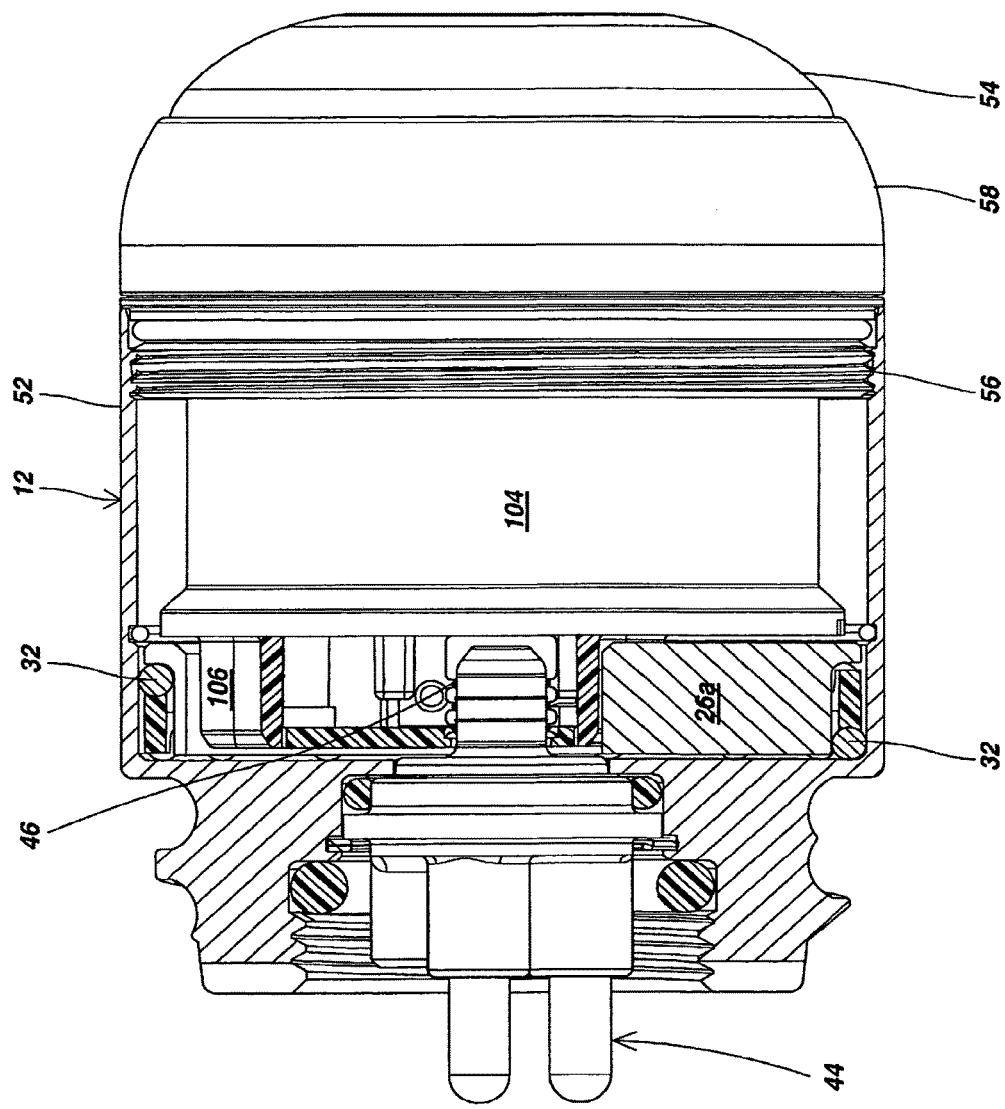
FIG. 9 is a part sectional, part side elevation view of the assembled self-leveling camera head of FIG. 1 illustrating further details thereof.
Figure 10:
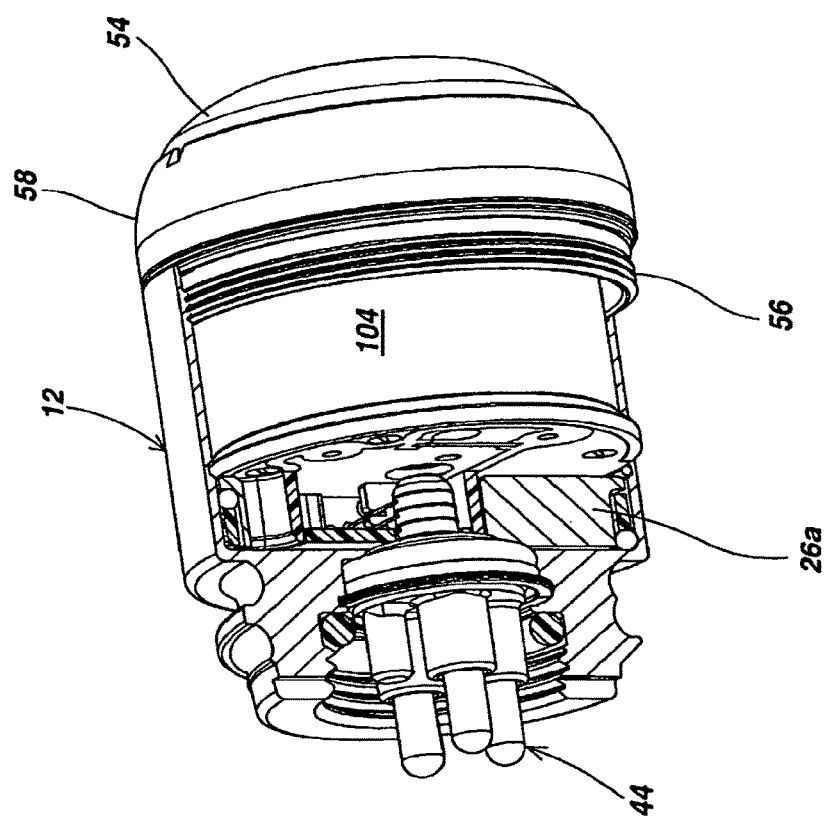
FIG. 10 is an isometric view similar to FIG. 9.

The circuit board assemblies 48 and 50 (FIGS. 2B and 11) are mounted in spaced apart opposing relationship inside the micro slip wire base 106, behind the micro slip wire cap 108. Each of the circuit board assemblies 48 and 50 supports the proximal or inner ends of three of the straight, resilient contact brushes 46, the intermediate portions of which ride against corresponding ones of the micro silver graphite rings 76, 78 and 80 as best seen in FIGS. 9 and 11. The distal or free outer ends 46a (FIG. 11) of the contact brushes 46 are retained from moving outward during installation to maintain contact force on the rings 76, 78 and 80 but are allowed to move and slide perpendicularly. As each contact brush 46 is bent and loaded against its corresponding ring it shortens and must be free to move at one end to prevent breakage or damage and to maintain even and compliant contact force. Spaced apart vertical guide members 112 made of suitable insulating dielectric material engage and ensure proper alignment of the contact brushes 46. There are a total of six contact brushes 46 and they are arranged in three pairs. The contact brushes 46 of each pair run on the opposite sides of a corresponding one of the silver graphite contact rings 76, 78 and 80. Use of redundant pairs of opposing contact brushes 46 helps eliminate video noise due to impacts and vibration. The contact brushes 46 must flex during installation and also during operation, and they are spring-loaded. The circuit board assemblies 48 and 50 are identical. Only the proximal ends of the contact brushes 46 are soldered to corresponding ones of the circuit board assemblies 48 and 50. The guide members 112 hold the intermediate segments of the contact brushes 46 in proper position and alignment. It does not matter which end of each of the contact brushes 46 is soldered, however, it is important that the intermediate segment of each of the contact brushes 46 is free to slide up and down in a guide slot formed in the corresponding one of the guide members 112. This arrangement helps keep the contact brushes 46 from being bent when the assemblies 42 and 44 are plugged together.

FIG. 12 illustrates a system 200 for inspecting a subterranean pipe P with a camera head 202, electronically re-orienting images of the inside of the pipe, and showing the images on a display 204. The images may be recorded on a VCR 206 or other recording device such as a DVD recorder. A camera module assembly 208 receives power through a video push cable 210 and sends video signals through the video push cable 210. The video push cable 210 may be of the type disclosed in U.S. Pat. No. 5,808,239 granted to Mark S. Olsson, the entire disclosure of which is hereby incorporated by reference. In this embodiment, it is not necessary for the camera module assembly 208 to be rotatable within the outer housing of the camera head 202, thereby eliminating the need for the leveling weight assembly 26 and the slip ring assembly.

The image sensor in the camera module assembly 208 may function with systems employing EIA, NTSC, CCIR, PAL and other standard analog or digital video signal formats. A stainless steel coil spring 212 surrounds the distal end of the push cable 210 and is coupled between the rear end of the video camera head 202 and a termination assembly 214. The coil spring 212 provides the desirable amount of flexibility to permit the video camera head 202 to negotiate tight turns inside of the pipe P. Stainless steel aircraft cables 216 connect the rear of the video camera head 202 to the termination assembly 214 to facilitate removal of the video camera head 202 in case it gets stuck inside the pipe P. In the presently preferred design, only a single aircraft cable is used. Deformable plastic fins 218 are clamped around the coil spring 212 to center the camera head 202 inside of the pipe P. Further details of the camera head 202 may be found in co-pending U.S. patent application Ser. No. 09/506,181 filed Feb. 27, 2000 of Mark S. Olsson et al., the entire disclosure of which is hereby incorporated by reference.

The push cable 210 (FIG. 12) is wound about a push reel 220 which can be rotated to pay out or take in the push cable 210. Further details of the push reel 220 are disclosed in U.S. Pat. No. 6,545,704 granted Apr. 8, 2003 to Mark S. Olsson et al., the entire disclosure of which is hereby incorporated by reference. At the proximal end of the push cable 210 the video, power and ground conductors within the push cable 210 are coupled to a slip ring assembly (SRA) 222. Other conductor schemes can be utilized including a two wire system of modulated video on power and a ground. The SRA 222 has an integral position encoder, such as that disclosed in co-pending U.S. patent application Ser. No. 10/799,473 filed Mar. 11, 2004 of Mark S. Olsson et al., the entire disclosure of which is hereby incorporated by reference. The video, power and ground conductors from the SRA 222 are connected to an electronic processing circuit 224. The video signals from the camera head 202 and the output signal from the position encoder within the SRA 222 are processed by the processing circuit 224 so that real time video images of the interior of the pipe P are shown on the display 204 with overlaid alphanumeric distance, time and/or date information.

Electromagnetic signals are emitted by a flexible transmitter 226 (FIG. 12) within the coil spring 212 for detection by a portable hand-held locator carried by a person traversing the ground under which the pipe P extends. The locator can determine and display a precise position of the camera head 202 within the pipe P. An example of such a transmitter is disclosed in co-pending U.S. patent application Ser. No. 10/061,887 filed Jan. 31, 2002 of Mark S. Olsson et al., the entire disclosure of which is hereby incorporated by reference. An example of a suitable transmitter circuit for driving the transmitter 226 and a suitable portable hand-held locator for detecting the electromagnetic signals emitted by the transmitter 226 are disclosed in co-pending U.S. patent application Ser. No. 10/308,752 filed Dec. 3, 2002 of Mark S. Olsson, the entire disclosure of which is hereby incorporated by reference.

Figure 13:
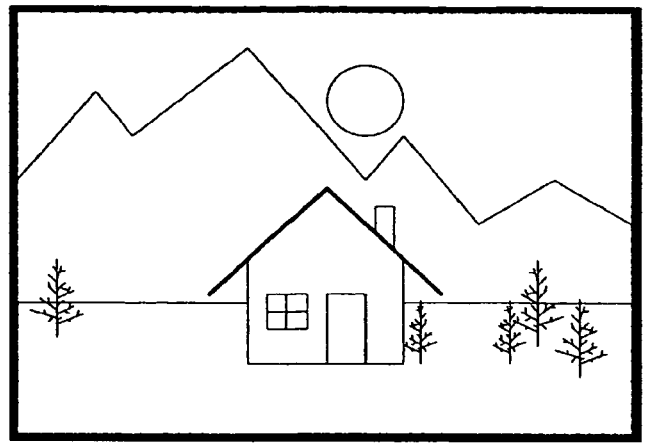
FIGS. 13-19 are a series of diagrammatic images of video displays illustrating the manner in which the video pipe inspection system of FIG. 12 electronically re-orients the video images.
Figure 14:
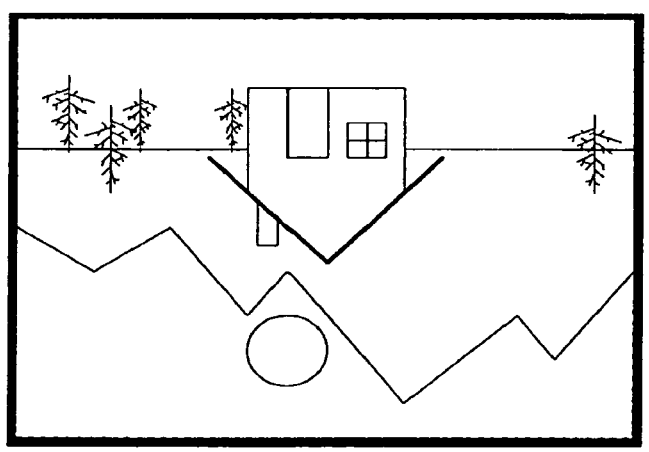
Figure 15:
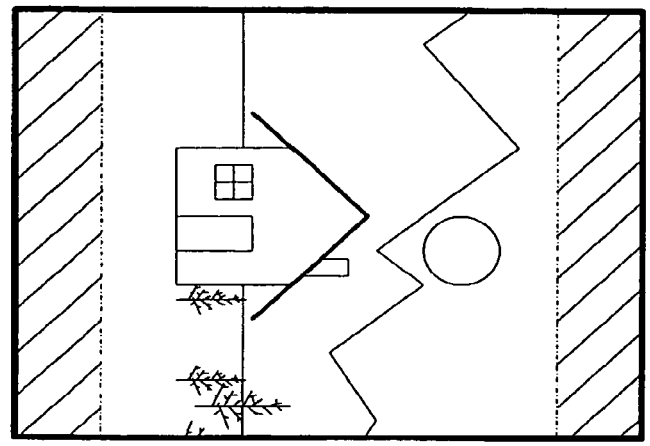

The processing circuit 224 (FIG. 12) can process the incoming source video in a number of ways to ensure that the images shown on the display 204 have the predetermined desired angular orientation as indicated by an orientation sensor 225 such as a two-axis accelerometer. The incoming video signal can be converted to a digital format, and then the processing circuit 224 can perform a rectangular rotation at ninety degree increments using the output signal from the orientation sensor 225. If the original video (FIG. 13) is rotated to one hundred and eighty degrees (FIG. 14), then remapping as in the case of a screen flip provides an optimal solution. If the video is rotated to ninety degrees or two hundred and seventy degrees, the video will be on end and can be presented in one of three ways:

1) The center region can be cropped such that the information that was on the right and left edges of the video source is lost, as illustrated by the cross-hatched regions in FIG. 15. However, the resolution and square pixel aspect ratio of the center region (typically the region of interest) is maintained. This is similar to matrix rotation at angles of ninety or two hundred and seventy degrees.

Figure 16:
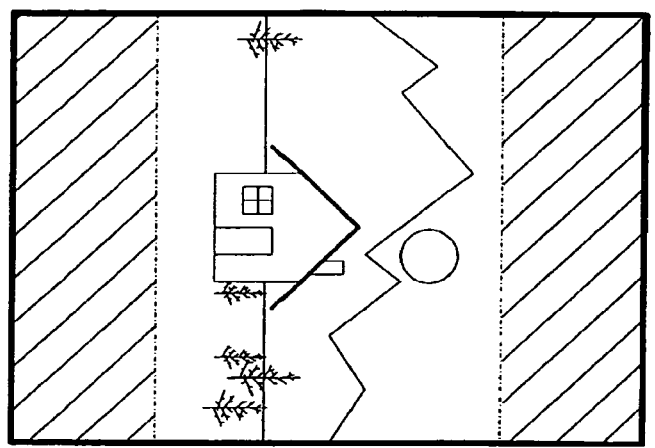

2) The video image can be reduced in size so that the horizontal dimension will fit on the display in a vertical orientation, i.e. the entire input image fits at right angles on the screen as illustrated in FIG. 16. This leaves significant "black space" on the right and left sides of the screen (vertical letter boxing), and lowers the resolution of the screen image, but maintains the square pixel ratio of the entire image. The black space is illustrated by cross-hatched regions in FIG. 16.

Figure 17:
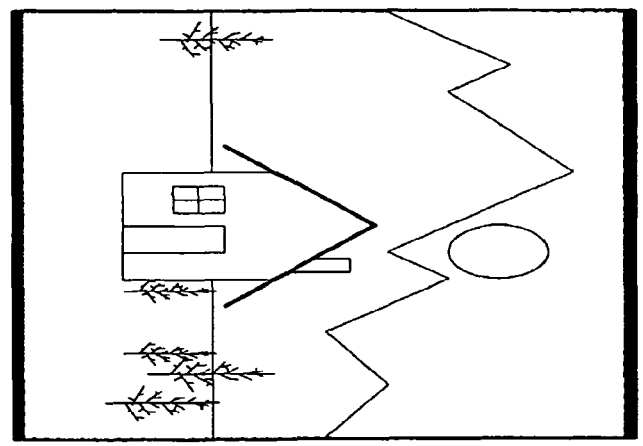

3) The display can be horizontally stretched (as is done commonly with "wide screen" 16:9 format TVs which take a 3:4 aspect ratio signal) as illustrated in FIG. 17. In this case, the original 3:4 signal is rotated on end, such that it will be in a 4:3 format, and then will be horizontally stretched out to a 3:4 again. This will yield a full screen image which was significantly distorted in aspect ratio.

Figure 18:
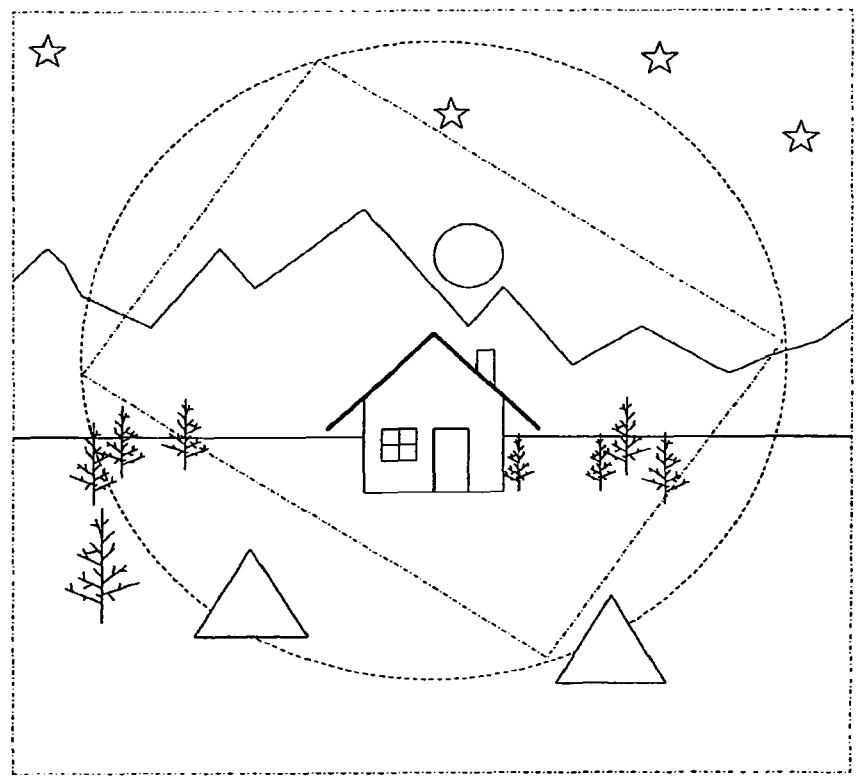
Figure 19:
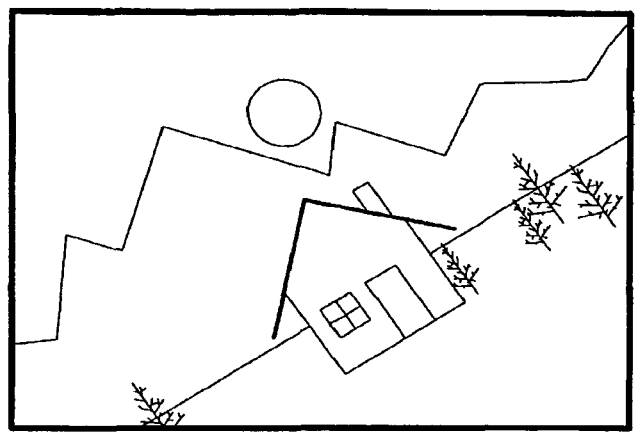

Another approach to image reorientation by the processing circuit 224 utilizes a high resolution image sensing device in the camera module assembly 208. This high resolution image sensing device has a linear resolution in both the vertical and horizontal directions greater than resolution of the diagonal of the image to be displayed. For instance, if an image sensing device with a 1,000×1,000 element sensor array is used to capture the image, and the display device only needs 640×480 pixels, then the 640×480 sub-image (which has a diagonal resolution (square root of sum of squares) of 800 elements) can be rotated within the source image to any angle, without loss of resolution or corruption of aspect ratio. The entire output of the high resolution image sensing device is sent to a video processor in the processing circuit 224 that selects and re-maps the elements within the rotated rectangular clipping region, and converts them into an analog or digital output format with a 3:4 aspect ratio, at full display device resolution as illustrated in FIGS. 18 and 19. This approach has a number of advantages. It allows for rotation to any angle as in the matrix operation above, but does not lose information in the cropping, and thus does not have "letterboxing." It also retains the aspect ratio of the source image as in the screen flip above, but allows for arbitrary rotation. It is also less computationally intense than matrix rotation.

There are further capabilities and advantages of utilizing an "oversized" image sensing device. Motion compensation is possible. This type of processing is commonly done with commercially available camcorders. It is done by re-mapping the image output rectangle within an oversized imager, such that the object of interest stays at the same location in the output video, even if there is vertical or horizontal motion in the source. This is done by x and y translation, and no rotation is required. With a higher resolution image sensing device it is possible to perform a sub-sampling or over-sampling of the image sensing device output to yield an electronic zoom in or out without loss of resolution. By changing the position of the output image rectangle within the image sensing device, it is possible to perform an electronic pan and tilt by specifying what region of the image sensing device is to be outputted. The entire oversized source image can be captured at any time as a high resolution still image and stored and processed at a later time. The video signal comprises a sequence of low resolution frames, and the processing circuit 224 is capable of selectively generating, automatically at predetermined intervals or upon operator command, one or more high-resolution still images for storage or display.

The diameter of the field of view of the lens assembly, such as 22 (FIG. 1), only needs to cover the diagonal of the rotated sub-sampled region. This means that the higher resolution image of the entire frame can be "port-holed", i.e. vignetted. The camera head 202 (FIG. 12) may be used for inspection applications, where the orientation of the camera may not be "earth normal." The camera head 202 can report back its orientation via the orientation sensor 225 to a video rotation unit in the processing circuit 224, and the image can be automatically rotated to make the output image "normal" (with respect to earth down), without regard to the orientation of the camera. There are a number of sensor technologies that may be used within the camera head 202 to facilitate the directional sensing of earth normal, including but not limited to accelerometers; tilt indicators including hanging mass, conductive ball, bubble (including conductive, thermal, ultrasonic and other); gyroscopes and other inertial systems; and/or single or multi-axis magnetic compasses including hall effect, flux gate, GMR, and others. A combination of such sensors could be used. Further, clues within the video could be used to determine earth normal—for instance flowing water could be an indicator of the bottom of scene and therefore earth normal, or objects scattered on a plane could be assumed to be on the ground, and therefore likely earth normal.

Thus, the orientation of the camera head 202 with respect to earth could be determined either at the camera head via sensors, by the camera module assembly 208, by video cues, or by the video processor in the processing circuit 224 using video cues. If the camera head 202 makes the earth normal determination, then it can transmit the information back to the controller/video processor by means including, but not limited to, encoding data into the video stream, having a separate carrier along with the base-band or modulated video which encodes the angle, transmitting the angle on a separate conductor, modulation on the power line or transmitting the angle information via some other wired or wireless technology. The image could also be rotated in response to operator commands.

While mechanical and electronic embodiments of our self-leveling camera head have been described in detail, it should be apparent to those skilled in the art that modifications can be made to the same without departing from the spirit of our invention. For example, instead of a removable coupling between the leveling weight assembly 26 (FIG. 2C) and the camera module assembly 16 (FIG. 1) that relies upon an inter-fitting key, other forms of coupling means could be employed including, but not limited to, gears, cams, pulleys, screw threads, drive shafts, fluid, or magnetic couplings.

As another example, the slip ring assembly could be arranged so that the silver graphite rings 76, 78 and 80 (FIG. 3) are mounted to the camera module assembly 16 and the contact brushes 46 (FIG. 9) are mounted to the connector assembly 44. The advantages of one aspect of our invention are achieved by having a slip ring assembly with first and second portions that can removably axially plug into one another, with the first portion being mounted for rotation with the camera module assembly 16 and the second portion fixedly mounted in the outer housing 12. This allows for separation of the slip ring assembly to permit the camera module assembly 16 to be removed from the forward end of the outer housing 12.

As still another example, the axis of rotation of the camera module assembly 16 and the axis of rotation of the leveling weight assembly 26 could be spaced from each other, and one or both of these axes could be spaced from the central axis 14 of the outer housing 12. Other sources of illumination besides the LEDs 24 (FIG. 2B) can be utilized such as incandescent lamps. In the embodiment of our camera head illustrated in FIGS. 1-11, the rotational axes of the leveling weight assembly 26 and the camera module assembly 16 substantially coincide with one another, and also substantially coincide with the central axis of the outer housing 12 for compactness and simplicity. However, due to the limitations imposed by manufacturing tolerances, as a practical matter, the axes of rotation of the leveling weight assembly 26, the camera module assembly 16 and the central axis 14 of the outer housing 12 cannot be exactly identical.

Our system for electronically re-orienting the video images is subject to a wide variety of modifications not described above. For example, the orientation information from the orientation sensor 224 (FIG. 12) could be saved and then processed later when the video images were displayed so that the images could be properly oriented at that time, instead of performing the orientation in real time. Our camera head can not only be connected to the distal end of a semi-rigid push cable such as the push cable 210 but may also be towed on the end of a so-called tractor cable. Moreover, the concepts described herein may be utilized in a wide variety of industrial applications not associated with pipe inspection such as assembly line monitoring. Therefore, the protection afforded our invention should only be limited in accordance with the scope of the following claims and their equivalents.

The invention claimed is:

1. A camera head comprising:
a cylindrical outer housing;
an illumination window positioned at the front end of the cylindrical housing assembly;
a lens assembly for focusing images or video from in front of the cylindrical housing assembly;
a high strength scratch resistant material window positioned in front of the lens assembly in a central aperture within the illumination window;
a camera module assembly, including an image sensor, supported inside an interior opening in the cylindrical housing assembly behind the lens assembly; and
a slip ring assembly removably coupled to the camera module assembly, the slip ring assembly including:
a plurality of elongate conductive contact brushes having proximal ends soldered to spaced apart opposing circuit board assemblies; and
a plurality of micro silver graphite contact rings electrically coupled to corresponding ones of the contact brushes.

2. The camera head of claim 1 wherein the illumination window is made of a transparent plastic.

3. The camera head of claim 1, further comprising a plurality of LEDs mounted within the enclosure cylindrical outer housing assembly for illuminating a field of view of the camera head through the illumination window.

4. The camera head of claim 1, wherein the scratch resistant material window comprises a sapphire material.

5. The camera head of claim 1, wherein the slip ring assembly is configured as a two part user-removable assembly for facilitating camera servicing.

6. The camera head of claim 1, wherein the lens assembly is a user adjustable lens assembly for adjusting the focus of the lens to the image sensor.

7. The camera head of claim 6, wherein the lens assembly is adjusted using a threaded coupling mechanism.

8. A self-leveling pipe inspection camera system, comprising:
a camera head comprising:
a substantially cylindrical outer housing;
an illumination window positioned at the front end of the cylindrical housing assembly;
a lens assembly for focusing images or video from in front of the cylindrical housing assembly;
a high strength scratch resistant material window positioned in front of the lens assembly in a central aperture within the illumination window;
a camera module assembly including an image sensor supported inside an interior opening in the cylindrical housing assembly behind the lens assembly;

a slip ring assembly removably coupled to the camera module assembly, the slip ring assembly including:

a plurality of elongate conductive contact brushes having proximal ends soldered to spaced apart opposing circuit board assemblies; and a plurality of micro silver graphite contact rings electrically coupled to corresponding ones of the contact brushes;

an angular orientation sensor;

an LED light assembly including a plurality of LED lighting elements positioned to provide light to an area being imaged by the high resolution image sensor;

a removable connector at an opposite end of the camera head from the transparent window including an attachment mechanism for mechanically coupling the camera head to a push-cable for deployment in a pipe, and an electrical connection for coupling an output signal from the high resolution image sensor and an orientation signal from the angular orientation sensor to the push-cable for transmission of the output signal to a pipe inspection system camera control unit; and a processing circuit for receiving the output signal from the high resolution image sensor and the orientation signal from the angular orientation sensor and providing an output image at a different resolution than the resolution of the output of the high resolution image sensor and adjusted to a predetermined desired angular orientation.

9. The system of claim 8, wherein the high strength scratch resistant material is sapphire.

10. The system of claim 8, further comprising a modular user-removable slip-ring assembly coupling an output of the camera module assembly to electrical terminals of the removable connector.

11. The system of claim 10, wherein the modular user-removable slip-ring assembly is a two part user-removable assembly for facilitating camera servicing.

12. The system of claim 8, wherein the lens assembly is a user adjustable lens assembly for adjusting the focus of the lens to the image sensor.

13. The system of claim 8, wherein the processing circuit provides the adjusted output image in an Earth normal orientation.

14. The system of claim 8, wherein the processing circuit includes instructions for execution on a processing element to digitally rotate a high resolution image to a predetermined orientation based at least in part on the received orientation signal.

15. The system of claim 8, wherein the angular orientation sensor comprises a multi-axis accelerometer.

* * * * *